(12) United States Patent
Zhang et al.

(10) Patent No.: US 10,829,755 B2
(45) Date of Patent: Nov. 10, 2020

(54) GENETICALLY ENGINEERED ARGININE DEIMINASE MODIFIED BY SITE-DIRECTED MUTAGENESIS

(71) Applicant: Jiangnan University, Wuxi (CN)

(72) Inventors: Tao Zhang, Wuxi (CN); Bo Jiang, Wuxi (CN); Hangyu Jiang, Wuxi (CN); Wanmeng Mu, Wuxi (CN); Ming Miao, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 16/245,881

(22) Filed: Jan. 11, 2019

(65) Prior Publication Data

US 2019/0136219 A1  May 9, 2019

Related U.S. Application Data

(63) Continuation of application No. PCT/CN2017/113162, filed on Nov. 27, 2017.

(30) Foreign Application Priority Data

Jan. 23, 2017 (CN) .......... 2017 1 00580551

(51) Int. Cl.
*C12N 9/78* (2006.01)
*C12Q 1/34* (2006.01)
*C12P 13/10* (2006.01)

(52) U.S. Cl.
CPC ............ *C12N 9/78* (2013.01); *C12P 13/10* (2013.01); *C12Q 1/34* (2013.01); *C12Y 305/03006* (2013.01); *C12N 2800/101* (2013.01)

(58) Field of Classification Search
None
See application file for complete search history.

(56) References Cited

FOREIGN PATENT DOCUMENTS

| CN | 101812438 A | 8/2010 | |
|---|---|---|---|
| CN | 102061283 A | 5/2011 | |
| CN | 102703339 A | 10/2012 | |
| CN | 103923898 A | 7/2014 | |
| CN | 104560927 A | 4/2015 | |
| CN | 104726478 A | 6/2015 | |
| CN | 106591270 A | 4/2017 | |
| WO | WO-0244360 A2 * | 6/2002 | ..... C12Y 305/03006 |
| WO | 2015143006 A1 | 9/2015 | |

* cited by examiner

*Primary Examiner* — Paul J Holland
(74) *Attorney, Agent, or Firm* — IPro, PLLC

(57) ABSTRACT

A genetically engineered arginine deiminase reconstructed by site-directed mutagenesis belongs to the technical field of genetic engineering technology. Its amino acid sequence is shown as SEQ ID No. 1. In the amino acid sequence of the arginine deiminase reconstructed by site-directed mutagenesis, glycine at position 264 is mutated to proline, compared to an amino acid sequence of native arginine deiminase. Compared with wild type enzyme, the effective pH range effect of the mutated arginine deiminase according to the present invention is broadened to a certain extent, and especially a good enzyme activity is achieved at physiological pH 7.4. With the broadening of the effective pH effect range, the mutant enzyme still has higher stability under the condition of pH 5.5-7.5. Therefore, the problem that the arginine deiminase generally is low in enzymatic activity and short in half-life in vivo under physiological conditions in clinical application for tumor therapy is solved, and a good condition for using the enzyme and an encoding gene thereof for clinical treatment is created.

11 Claims, 2 Drawing Sheets

Specification includes a Sequence Listing.

GENETICALLY ENGINEERED ARGININE DEIMINASE MODIFIED BY SITE-DIRECTED MUTAGENESIS

TECHNICAL FIELD

The disclosure herein relates to a genetically engineered arginine deiminase modified by site-directed mutagenesis, belonging to the technical field of genetic engineering.

BACKGROUND

Arginine deiminase (EC 3.5.3.6) is referred to as ADI for short, which catalyzes the first reaction in an arginine metabolic pathway in microorganisms, that is, the arginine is hydrolyzed to produce citrulline and ammonia. Arginine deiminase is widely sourced, and is currently found in bacteria, archaea and some eukaryotic cells. At the same time, the properties of arginine deiminase from different sources are quite different.

At present, scholars studying arginine deiminase at home and abroad mainly apply the enzyme to the preparation of citrulline and the treatment of diseases. Among them, in the medicine field, arginine deiminase has good performance in inhibiting arginine-deficient tumor, breast cancer and liver cancer cells and treating leukemia as an alternative to L-asparaginase. ADI-PEG-20, developed by Phoenix Pharmaceuticals Inc., USA, has been tested in phase III human clinical trials of liver cancer worldwide. Results show that ADI-PEG-20 can prolong the average life of patients by 76%.

Up to now, arginine deiminase has not been widely used as pharmaceutical enzyme due to problems such as low enzyme activity under physiological conditions, short half-life in vivo, weak substrate affinity and the like. Therefore, it is especially important to improve the enzymatic properties through molecular modification.

Site-directed mutagenesis is one of the main means of molecular modification, and refers to a technique of introducing a specific base pair at a designated site of a DNA fragment of interest, thereby changing an encoded amino acid sequence. Compared with other strategies to improve enzymatic properties, site-directed mutagenesis has the advantages of being more rapid, direct and cost-effective, and it is one of the means of genetic modification commonly used in laboratories.

SUMMARY

The object of the present invention is to improve the enzyme activity and stability of modified arginine deiminase to some extent under the condition of physiological pH 7.4 by molecular modification of arginine deiminase, and to finally apply to the medicine field.

The technical solution of the present invention: An arginine deiminase mutant modified by site-directed mutagenesis, referred to as genetically engineered arginine deiminase, is obtained from an arginine deiminase gene of *Enterococcus faecalis* SK32.001 by using the site-directed mutagenesis technique, in which the amino acid sequence of the arginine deiminase mutant is SEQ ID No. 1, and the gene DNA of the arginine deiminase mutant modified by site-directed mutagenesis is encoded by a nucleotide sequence as shown in SEQ ID No. 2.

A recombinant plasmid comprises a DNA molecule.

A host cell comprises the DNA molecule or the recombinant plasmid.

The arginine deiminase mutant is constructed by transferring an arginine deiminase mutant plasmid containing an amino acid mutational site predicted by B-FITTER into an *Escherichia coli* BL21(DE3) host. Sequence verification confirms that a mutant Gly264Pro with the optimum pH and pH stability approaching physiological neutral pH 7.4 is obtained, in which glycine (Gly) at position 264 is mutated to proline (Pro).

A method for constructing the arginine deiminase mutant comprises the following steps:

performing a reverse PCR by using a recombinant plasmid derived from an arginine deiminase gene carried by an *E. coli* host as a template and using an oligonucleotide sequence having a mutational site as a primer so as to amplify the full length of the mutant plasmid; digesting with Dpn I restriction enzyme; transforming a PCR product treated by the Dpn I restriction enzyme into *E. coli* DH5α by heat shock, coating on a solid LB medium having kanamycin resistance and culturing; picking single colonies on the solid LB medium and inoculating into a liquid LB medium having kanamycin resistance, extracting a plasmid, and sequencing; transforming the plasmid with correct sequencing results into an *E. coli* BL21(DE3) competent cell to obtain a mutant, i.e., genetically engineered arginine deiminase.

Application of the arginine deiminase mutant: the arginine deiminase mutant is used for medicinal antitumor activity and related pharmacological activity studies.

Amino acid mutation is located inside an arginine deiminase protein structure, and the mutation can increase the hydrophobic interaction of protein.

The amino acid mutation is performed by replacing glycine at position 264 of arginine deiminase with proline, and a resulting single mutant is named Gly264Pro.

The present invention provides a method for constructing the arginine deiminase mutant, and the specific steps are as follows:

1. constructing a genetically engineered recombinant strain of arginine deiminase with pET-28a-c(+) as an expression vector and expressed in an expression host *E. coli* BL21(DE3);

2. designing a mutant primer, and performing site-directed mutagenesis on an arginine deiminase gene by reverse PCR to obtain a recombinant vector containing a mutated arginine deiminase gene sequence;

3. transforming the mutated recombinant vector into *E. coli* BL21(DE3) by heat shock, inducing expression, collecting thallus, and after ultrasonication of cells, performing protein separation and purification by using Ni-NTA to obtain mutated arginine deiminase.

The optimum pH and pH stability of the arginine deiminase mutant provided by the present invention are both shifted to a physiological neutral direction, the optimum pH is increased from original 5-5.5 to 5.5-7.5, and the pH stability range is shifted from 5.5-6.5 to 6.5-7.5. Therefore, the problem that wild type arginine deiminase is low in catalytic activity and stability under the condition of physiological pH 7.4 is solved, and favorable conditions for the application of the enzyme in the medicine field are thus created.

A gene arcA of the arginine deiminase used in the present invention is derived from an *Enterococcus faecalis* which can produce citrulline (strain number: CCTCC NO: M 2011465), is deposited in the China Center for Type Culture Collection (Address: Wuhan University, Wuhan, China), named SK32.001 (*Enterococcus faecalis* SK32.001), and has been published in Chinese patent CN 102433290 A.

DETAILED DESCRIPTION

Figure 1:
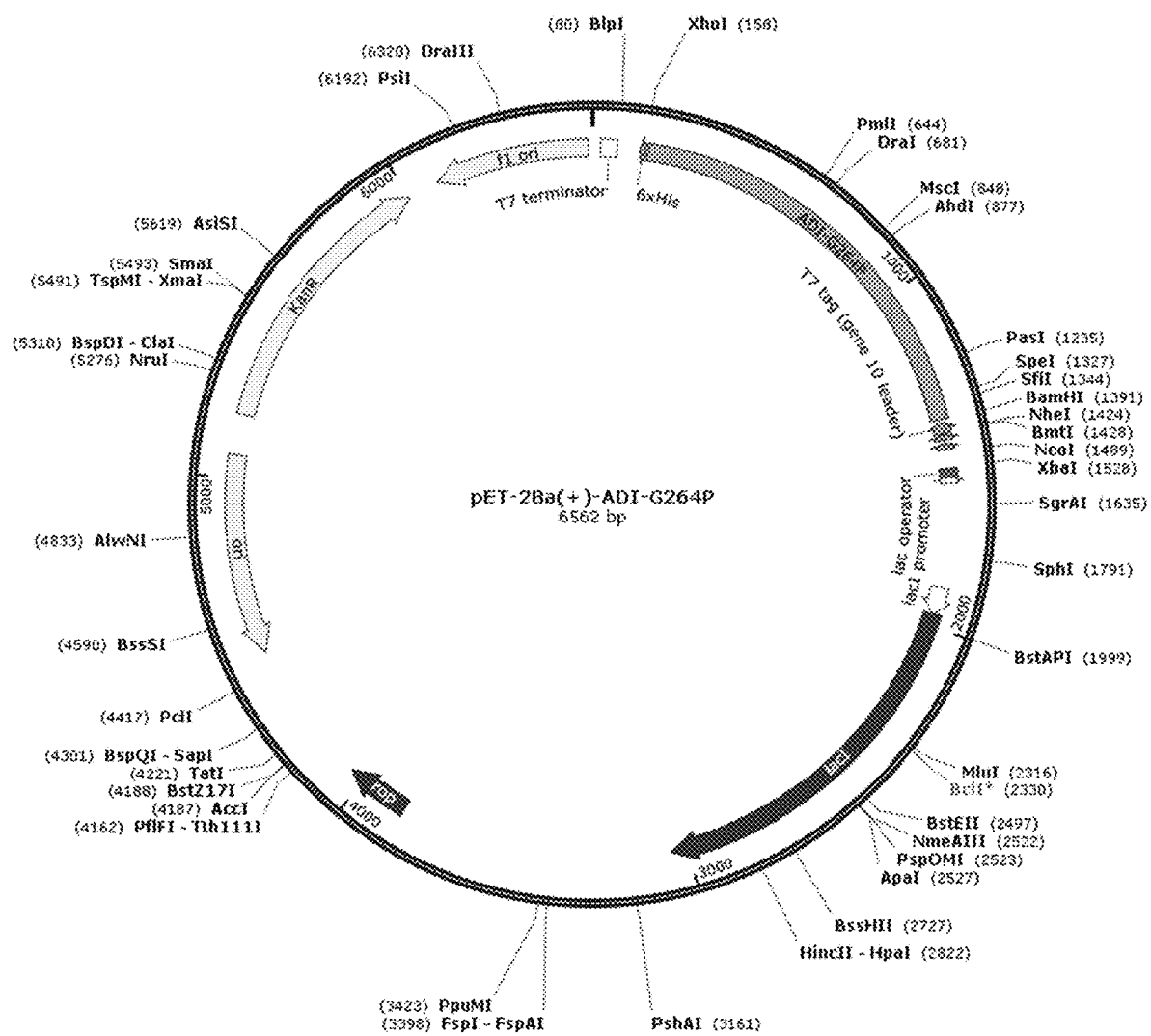
FIG. 1: Construction map of recombinant plasmid pET-28a-ADI.

The present invention is further clarified below by examples, and the following examples are intended to illustrate and not to limit the scope of the present invention.

Materials and reagents: Restriction enzymes, Solution I ligase, PCR reagents and the like were all purchased from TaKaRa Biotechnology Co., Ltd.; plasmid extraction kit, genome extraction kit, agarose purification kit, $E.$ $coli$ DH5α, BL21(DE3) strains and primers were all purchased from Sangon Biotech (Shanghai) Co., Ltd.; other reagents were all analytically pure reagents purchased domestically or abroad.

EXAMPLE 1: CONSTRUCTION OF RECOMBINANT PLASMID $Enterococcus$ $faecalis$ SK32.001 was cultured to the mid-exponential growth phase. 2 mL of a bacteria solution was centrifuged at 10000 r/min for 10 min. Supernatant was discarded. After lysozyme treatment for 30 min, genomic DNA was extracted according to a kit instruction.

The following primers were designed for amplification of arcA:

```
FADI-2:
                                    (SEQ ID NO: 5)
5'-CGCGGATCCA TGAGTCATCC AATTAATGT-3'
(containing BamH I restriction site),
and RADI-2:
                                    (SEQ ID NO: 6)
5'-CCGCTCGAGT TAAAGATCTT CACGGT-3'
(containing Xho I restriction site).
```

PCR amplification conditions: denaturation at 95° C. for 3 min, 30 cycles (95° C. for 30 s, 55° C. for 30 s, and 72° C. for 210 s) and finally extension at 72° C. for 2 min.

After purification of an amplified product, the PCR product and a vector pET-28a-c(+) were double-digested with BamH I and Xho I, and enzyme-digested products were separately recovered. The products were ligated with Solution I ligase at 16° C. for 2 h and transformed into DH5α cells by heat shock. After transformants were grown on a plate, single colonies were picked into an LB medium, and the plasmid was extracted. The recombinant plasmid pET-28a-ADI was verified by enzyme digestion. The plasmid was transformed into BL21(DE3) cells to obtain BL21 (DE3)/pET-28a-ADI engineered bacteria.

EXAMPLE 2: SITE-DIRECTED MUTAGENESIS

Primer design was performed based on the encoding gene encoding arcA in $Enterococcus$ $faecalis$ SK23.001.

```
G264P-forward primer:
                                    (SEQ ID NO: 7)
5'-CTTGGCTTTT GATATCCCTG AACATCGTAA ATTC-3',
and G264P-reverse primer:
                                    (SEQ ID NO: 8)
5'-GATATCAAAA GCCAAGATAT TTTTGAATCC TA-3'.
```

The underlined portion represents a codon corresponding to glycine at position 264 encoded by the mutant gene. The PCR amplification system is:

| | |
|---|---|
| 10 X Reaction Buffer | 5 |
| dNTP mix | 1 |
| Forward primer (100 ng/μL) | 1.25 |
| Reverse primer (100 ng/μL) | 1.25 |
| Template pET-28a-ADI (10 ng) | 2 |
| PfuTurbo DNA polymerase (2.5 U/μL) | 1 |
| ddH$_2$O | 38.5 |
| Total volume | 50 |

After PCR amplification, 1 μL of Dpn I restriction enzyme (10 U/μL) was added into a reaction solution, and a template was eliminated by incubation at 37° C. for 1 h. A PCR product was transformed into $E.$ $coli$ DH5α cells and coated on a plate. Single colonies were picked to an LB medium, a plasmid was extracted, and a correct mutant plasmid was obtained by sequencing. The successfully constructed mutant plasmid was transformed into $E.$ $coli$ BL21(DE3) to obtain a mutant strain BL21(DE3)/pET-28a-ADIG264P.

EXAMPLE 3: EXPRESSION AND PURIFICATION OF WILD ENZYME AND MUTANT ENZYME

BL21(DE3)/pET-28a-ADI and pET-28a-ADIG264P single colonies were picked up and cultured in an LB medium containing 0.5 mmol/L kanamycin at 37° C. and 200 r/min for 12 h, then transferred into an LB medium containing 0.5 mmol/L kanamycin and cultured at 37° C. and 200 r/min until OD$_{600}$ fell within in the range of 0.5-0.7. 1 mmol/L IPTG was added and the mixture was induced under the conditions of 28° C. and 200 r/min for 9 h.

Fermentation broth was centrifuged at 10000 r/min and 4° C. for 10 min, and then supernatant was discarded. Washing with a phosphate buffer was performed twice, thallus was suspended by adding 15-20 mL of phosphate buffer, and ultrasonicated for 15 min (power 22 W, ultrasonication for 1 s, and intermittence for 2 s). Centrifugation was performed under the conditions of 4° C. and 10000 r/min for 10 min, and supernatant (namely crude enzyme solution) was collected, and filtered through a hydrophilic membrane with a pore size of 0.22 μm.

An Ni$^{2+}$chelate agarose resin column was pre-equilibrated with a Binding Buffer; the crude enzyme solution was added, and the column was equilibrated with the Binding Buffer and a Washing Buffer respectively; enzyme was eluted with an Elution Buffer and recovered; the recovered enzyme solution was dialyzed in a dialysis buffer and then stored in a refrigerator at 4° C.

Formulation of the Involved Buffers 1. phosphate buffer (PB): 50 mmol/L, pH 5.5;
2. Binding Buffer: 50 mmol/L PB, 500 mmol/L NaCl, pH 7.0;
3. Washing Buffer: 50 mmol/L PB, 500 mmol/L NaCl, pH 7.0, 50 mmol/L imidazole;

4. Elution Buffer: 50 mmol/L PB, 500 mmol/L NaCl, pH 7.0, 500 mmol/L imidazole;
5. Dialysis buffer: 50 mmol/L PB, pH 5.5, 10 mmol/L EDTA.

EXAMPLE 4: DETERMINATION OF OPTIMUM pH AND pH STABILITY OF WILD ENZYME AND MUTANT ENZYME

Enzyme activity assay method: 0.49 mL of 50 mmol/L PB buffer was added into 0.5 mL of a substrate L-arginine (concentration: 10 g/L) and heat-insulated at 45° C. for 5 min, and then 0.01 mL of an enzyme solution was added. A reaction was carried out at 45° C. for 10 min and terminated by boiling for 10 min. A reaction solution was centrifuged, supernatant was removed, and the content of citrulline was determined.

Definition of enzyme activity: The amount of enzyme required to produce 1 µmol $L^{-1}$ citrulline within 1 min is defined as one enzyme activity unit (U).

Determination of citrulline content: high performance liquid chromatography: Angilent 1200; chromatographic column: Hypersil ODS (5 µm, 4.0 mm×250 mm); mobile phase A: 2 L of water, 13 g of sodium acetate trihydrate, 0.4 mL of triethylamine, 5 mL of tetrahydrofuran, pH 7.2±0.5; mobile phase B: 2 L, 15 g of sodium acetate trihydrate, water/methanol/acetonitrile (volume ratio 1:2:2), pH 7.2±0.5; gradient elution with mobile phases A and B, total flow rate: 1.0 mL/min; column temperature: 40° C.; injection volume: 10 µL; detector: ultraviolet detector; detection wavelength: 338 nm, emission wavelength 360 nm.

Optimum pH: Wild enzyme or mutant enzyme pre-preserved in 50 mM of PB buffer at pH 4.0-7.5 was placed in a water bath at 45° C. A reaction was carried out for 10 min and then terminated immediately upon boiling. PH stability: The same concentration of wild enzyme and mutant enzyme were pre-preserved in a buffer at pH 4.0-7.5 and 4° C. for 12 h, and then the enzyme activity was measured under the condition of 45° C.

Figure 2:
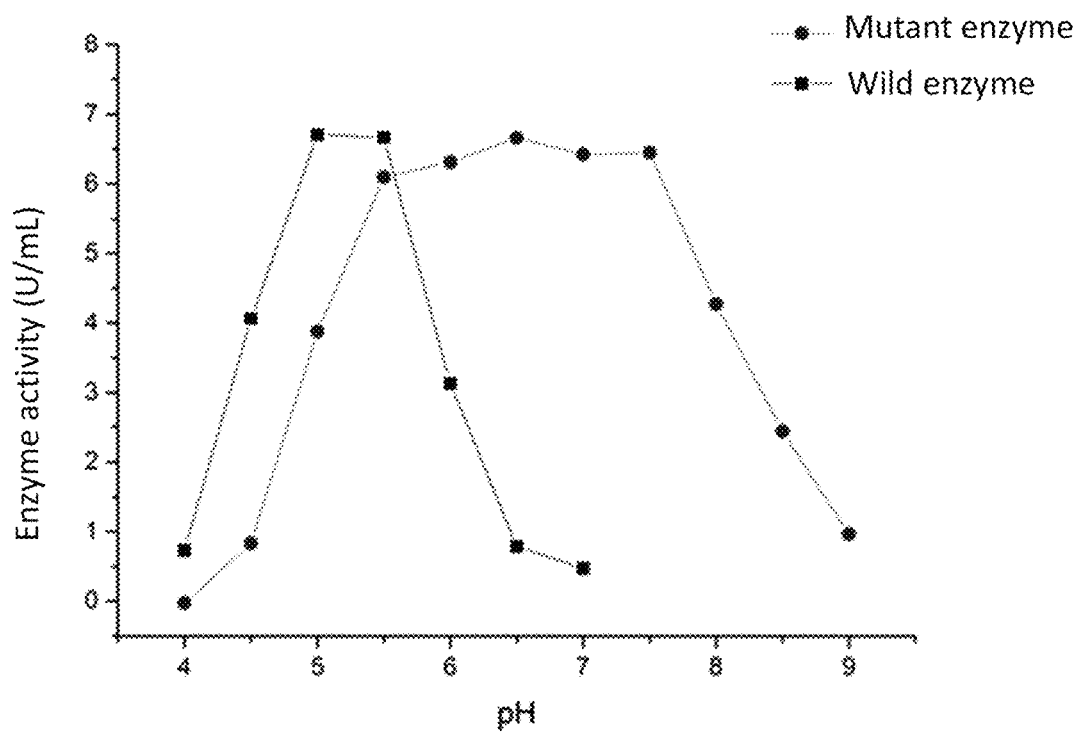
FIG. 2: A graph showing optimal pH changes of wild enzyme and mutant enzyme.
Figure 3:
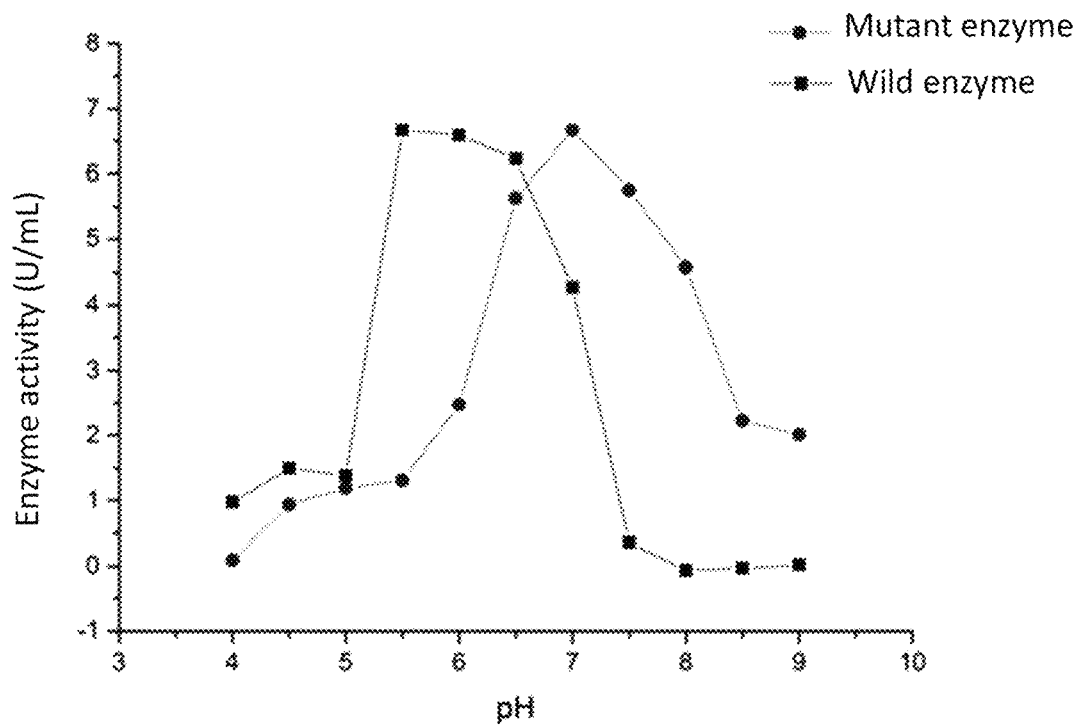
FIG. 3: A graph showing pH stability changes of wild enzyme and mutant enzyme.

Results obtained are shown in FIG. 2: the effective pH range of the mutant enzyme is broadened and shifted to neutral compared to the wild enzyme. As shown in FIG. 3: the mutant enzyme is more stable when preserved at near-neutral pH compared to the wild enzyme.

What is claimed is:

1. An arginine deiminase mutant, comprising the amino acid sequence of SEQ ID NO: 1, wherein the mutant possesses improved enzyme activity and stability relative to a wild type arginine deiminase of Enterococcus faecalis.

2. The arginine deiminase mutant of claim 1, wherein the mutant is encoded by the nucleotide sequence of SEQ ID NO: 2.

3. A host cell comprising the nucleotide sequence of SEQ ID NO: 2 encoding the arginine deiminase mutant of claim 1.

4. The host cell of claim 3, wherein the host cell is an *Escherichia coli* cell.

5. The host cell of claim 4, wherein the host cell is an *E. coli* BL21(DE3) cell.

6. A method of treating a subject who has an arginine-deficient tumor, comprising:
   administering a pharmaceutically effective amount of a composition comprising the arginine deiminase mutant of claim 1 to the subject.

7. A method of treating leukemia in a subject, comprising:
   administering a pharmaceutically effective amount of a composition comprising the arginine deiminase mutant of claim the subject.

8. A method of enzymatically producing citruline, comprising adding the arginine deiminase mutant of claim 1 to a solution comprising arginine under conditions in which the mutant catalyzes the conversion of arginine to citruline, thereby producing citruline.

9. The method of claim 6, wherein the arginine-deficient tumor is a breast cancer tumor.

10. The method of claim 6, wherein the arginine-deficient tumor is a liver cancer.

11. The arginine deiminase mutant of claim 1, wherein the stability of the mutant is increased by at least 2 pH units at 45° C. as compared to a wild type arginine deiminase enzyme from *Enterococcus faecalis*.

* * * * *

SEQUENCE LISTING

```
<160> NUMBER OF SEQ ID NOS: 8

<210> SEQ ID NO 1
<211> LENGTH: 408
<212> TYPE: PRT
<213> ORGANISM: Artificial Sequence
<220> FEATURE:
<223> OTHER INFORMATION: Synthetic protein

<400> SEQUENCE: 1

Met Ser His Pro Ile Asn Val Phe Ser Glu Ile Gly Lys Leu Lys Thr
1               5                   10                  15

Val Met Leu His Arg Pro Gly Lys Glu Leu Glu Asn Leu Met Pro Asp
            20                  25                  30

Tyr Leu Glu Arg Leu Leu Phe Asp Asp Ile Pro Phe Leu Glu Lys Ala
        35                  40                  45

Gln Ala Glu His Asp Ala Phe Ala Glu Leu Leu Arg Ser Lys Asp Ile
    50                  55                  60

Glu Val Val Tyr Leu Glu Asp Leu Ala Ala Glu Ala Leu Ile Asn Glu
65                  70                  75                  80

Glu Val Arg Arg Gln Phe Ile Asp Gln Phe Leu Glu Glu Ala Asn Ile
            85                  90                  95

Arg Ser Glu Ser Ala Lys Glu Lys Val Arg Glu Leu Met Leu Glu Ile
            100                 105                 110

Asp Asp Asn Glu Glu Leu Ile Gln Lys Ala Ile Ala Gly Ile Gln Lys
        115                 120                 125

Gln Glu Leu Pro Lys Tyr Glu Gln Glu Phe Leu Thr Asp Met Val Glu
    130                 135                 140

Ala Asp Tyr Pro Phe Ile Ile Asp Pro Met Pro Asn Leu Tyr Phe Thr
145                 150                 155                 160

Arg Asp Asn Phe Ala Thr Met Gly His Gly Ile Ser Leu Asn His Met
            165                 170                 175

Tyr Ser Val Thr Arg Gln Arg Glu Thr Ile Phe Gly Gln Tyr Ile Phe
            180                 185                 190

Asp Tyr His Pro Arg Phe Ala Gly Lys Glu Val Pro Arg Val Tyr Asp
        195                 200                 205
```

```
Arg Ser Glu Ser Thr Arg Ile Glu Gly Gly Asp Leu Ile Leu Ser
210                 215                 220

Lys Glu Val Val Ala Ile Gly Ile Ser Gln Arg Thr Asp Ala Ala Ser
225                 230                 235                 240

Ile Glu Lys Ile Ala Arg Asn Ile Phe Glu Gln Lys Leu Gly Phe Lys
                245                 250                 255

Asn Ile Leu Ala Phe Asp Ile Pro Glu His Arg Lys Phe Met His Leu
                260                 265                 270

Asp Thr Val Phe Thr Met Ile Asp Tyr Asp Lys Phe Thr Ile His Pro
            275                 280                 285

Glu Ile Glu Gly Gly Leu Val Val Tyr Ser Ile Thr Glu Lys Ala Asp
290                 295                 300

Gly Asp Ile Gln Ile Thr Lys Glu Lys Asp Thr Leu Asp Asn Ile Leu
305                 310                 315                 320

Cys Lys Tyr Leu His Leu Asp Asn Val Gln Leu Ile Arg Cys Gly Ala
                325                 330                 335

Gly Asn Leu Thr Ala Ala Ala Arg Glu Gln Trp Asn Asp Gly Ser Asn
                340                 345                 350

Thr Leu Ala Ile Ala Pro Gly Glu Val Val Tyr Asp Arg Asn Thr
            355                 360                 365

Ile Thr Asn Lys Ala Leu Glu Glu Ala Gly Val Lys Leu Asn Tyr Ile
370                 375                 380

Pro Gly Ser Glu Leu Val Arg Gly Arg Gly Pro Arg Cys Met Ser
385                 390                 395                 400

Met Pro Leu Tyr Arg Glu Asp Leu
                405

<210> SEQ ID NO 2
<211> LENGTH: 1227
<212> TYPE: DNA
<213> ORGANISM: Artificial Sequence
<220> FEATURE:
<223> OTHER INFORMATION: Synthetic DNA

<400> SEQUENCE: 2
atgagtcatc caattaatgt attttctgaa atcggaaaat tgaaaacagt gatgttacat      60
cgtccaggta aggaattaga aaatttaatg ccagattatc tggagagact gttgtttgat     120
gatattccgt ttttagaaaa agcacaagca gaacatgatg catttgcaga gttgttacga     180
tcaaaagata tcgaagtggt ctatttagag gacttagctg ctgaagcgtt gattaatgaa     240
gaggtccgcc gacaatttat tgaccaattc ttagaagaag ccaatattcg cagcgaatca     300
gcaaaagaaa aagttagaga gttaatgtta gaaattgacg acaacgaaga actgattcaa     360
aaagcgattg ctggcattca aaaacaagaa ttacctaaat atgagcaaga ttttttaaca     420
gatatggttg aagcggatta ccattcatt attgatccaa tgcctaactt atacttcaca     480
cgtgataact tgcgacaat gggccacggg atttctttaa atcatatgta ttcagtaact     540
cgacaacggg aaaccatttt tgggcaatac atttttgatt atcatcctcg ttttgctgga     600
aaagaggttc ctagagtcta tgatcgttca gaatcaacca gaattgaagg tggcgatgaa     660
ttaattcttt caaagaagt ggtggccatt gggattctc aaagaacgga cgccgcgtca     720
attgaaaaaa ttgcgagaaa tattttttgaa caaaaattag gattcaaaaa tatcttggct     780
tttgatatcc ctgaacatcg taaattcatg catttagata ccgttttttac catgattgac     840 tatgataaat ttacgattca tccagaaatc gaaggcggct tggttgttta ctcgatcact     900
```

```
gaaaaagcag atggagacat ccaaattaca aaagaaaaag atacattaga taacatttta      960
tgcaaatact tgcatttaga caatgttcaa ttaatccgtt gcggcgctgg aaatttaacc     1020
gcagcagccc gggaacaatg gaacgacggt tcaaatacat tagcaattgc ccctggggaa     1080
gttgttgttt acgatcggaa tacgattacg aataaagcgc tagaagaagc aggcgtgaaa     1140
ttgaattaca ttccaggaag tgaactagta cgtggccgtg gtggccctcg ttgtatgagt     1200
atgccacttt accgtgaaga tctttaa                                          1227
```

<210> SEQ ID NO 3
<211> LENGTH: 408
<212> TYPE: PRT
<213> ORGANISM: Artificial Sequence
<220> FEATURE:
<223> OTHER INFORMATION: Synthetic protein

<400> SEQUENCE: 3

```
Met Ser His Pro Ile Asn Val Phe Ser Glu Ile Gly Lys Leu Lys Thr
  1               5                  10                  15

Val Met Leu His Arg Pro Gly Lys Glu Leu Glu Asn Leu Met Pro Asp
                 20                  25                  30

Tyr Leu Glu Arg Leu Leu Phe Asp Asp Ile Pro Phe Leu Glu Lys Ala
             35                  40                  45

Gln Ala Glu His Asp Ala Phe Ala Glu Leu Leu Arg Ser Lys Asp Ile
         50                  55                  60

Glu Val Val Tyr Leu Glu Asp Leu Ala Ala Glu Ala Leu Ile Asn Glu
 65                  70                  75                  80

Glu Val Arg Arg Gln Phe Ile Asp Gln Phe Leu Glu Glu Ala Asn Ile
                 85                  90                  95

Arg Ser Glu Ser Ala Lys Glu Lys Val Arg Glu Leu Met Leu Glu Ile
            100                 105                 110

Asp Asp Asn Glu Glu Leu Ile Gln Lys Ala Ile Ala Gly Ile Gln Lys
        115                 120                 125

Gln Glu Leu Pro Lys Tyr Glu Gln Glu Phe Leu Thr Asp Met Val Glu
    130                 135                 140

Ala Asp Tyr Pro Phe Ile Ile Asp Pro Met Pro Asn Leu Tyr Phe Thr
145                 150                 155                 160

Arg Asp Asn Phe Ala Thr Met Gly His Gly Ile Ser Leu Asn His Met
                165                 170                 175

Tyr Ser Val Thr Arg Gln Arg Glu Thr Ile Phe Gly Gln Tyr Ile Phe
            180                 185                 190

Asp Tyr His Pro Arg Phe Ala Gly Lys Glu Val Pro Arg Val Tyr Asp
        195                 200                 205

Arg Ser Glu Ser Thr Arg Ile Glu Gly Gly Asp Glu Leu Ile Leu Ser
    210                 215                 220

Lys Glu Val Val Ala Ile Gly Ile Ser Gln Arg Thr Asp Ala Ala Ser
225                 230                 235                 240

Ile Glu Lys Ile Ala Arg Asn Ile Phe Glu Gln Lys Leu Gly Phe Lys
                245                 250                 255

Asn Ile Leu Ala Phe Asp Ile Gly Glu His Arg Lys Phe Met His Leu
            260                 265                 270

Asp Thr Val Phe Thr Met Ile Asp Tyr Asp Lys Phe Thr Ile His Pro
        275                 280                 285

Glu Ile Glu Gly Gly Leu Val Val Tyr Ser Ile Thr Glu Lys Ala Asp
    290                 295                 300
```

```
Gly Asp Ile Gln Ile Thr Lys Glu Lys Asp Thr Leu Asp Asn Ile Leu
305                 310                 315                 320

Cys Lys Tyr Leu His Leu Asp Asn Val Gln Leu Ile Arg Cys Gly Ala
            325                 330                 335

Gly Asn Leu Thr Ala Ala Ala Arg Glu Gln Trp Asn Asp Gly Ser Asn
            340                 345                 350

Thr Leu Ala Ile Ala Pro Gly Glu Val Val Val Tyr Asp Arg Asn Thr
            355                 360                 365

Ile Thr Asn Lys Ala Leu Glu Ala Gly Val Lys Leu Asn Tyr Ile
            370                 375                 380

Pro Gly Ser Glu Leu Val Arg Gly Arg Gly Pro Arg Cys Met Ser
385                 390                 395                 400

Met Pro Leu Tyr Arg Glu Asp Leu
            405
```

<210> SEQ ID NO 4
<211> LENGTH: 1227
<212> TYPE: DNA
<213> ORGANISM: Artificial Sequence
<220> FEATURE:
<223> OTHER INFORMATION: Synthetic DNA

<400> SEQUENCE: 4

```
atgagtcatc caattaatgt attttctgaa atcgggaaat tgaaaacagt gatgttacat      60
cgtccaggta aggaattaga aaatttaatg ccagattatc tggagagact gttgttgat     120
gatattccgt ttttagaaaa agcacaagca gaacatgatg catttgcaga gttgttacga    180
tcaaaagata tcgaagtggt ctatttagag gacttagctg ctgaagcgtt gattaatgaa    240
gaggtccgcc gacaatttat tgaccaattc ttagaagaag ccaatattcg cagtgaatca    300
gcaaagaaa aagttagaga gttaatgtta gaaattgacg acaacgaaga acttattcaa    360
aaagcgattg ctggcattca aaaacaagaa ttacctaaat atgagcaaga atttttaaca    420
gatatggttg aagcggatta ccattcatt attgatccaa tgcctaactt atacttcaca    480
cgtgataact ttgcgacaat gggccacggg atttctttaa atcatatgta ttcagtaact    540
cgacaacggg aaaccatttt tgggcaatac atttttgatt atcatcctcg ttttgctgga    600
aaagaggttc ctagagtcta tgatcgttca gaatcaacca gaattgaagg tggcgatgaa    660
ttaattcttt caaagaagt ggtggccatt gggatttctc aaagaacgga cgccgcgtca    720
attgaaaaaa ttgcgagaaa tatttttgaa caaaaattag gattcaaaaa tatcttggct    780
tttgatatcg gtgaacatcg taaattcatg catttagata ccgttttac catgattgac    840
tatgataaat ttacgattca tccagaaatc gaaggcggct tggttgttta ctcgatcact    900
gaaaaagcag atggagacat ccaaattaca aagaaaaag atacattaga taacatttta    960
tgcaaatact tgcatttaga caatgttcaa ctaatccgtt gcggcgctgg aaatttaaca   1020
gcagcagccc gtgaacaatg gaacgacggt tcaaatatac tagcaattgc ccctggggaa   1080
gttgttgttt acgatcggaa tacgattacg aataaagcgc tagaagaagc aggcgtgaaa   1140
ttgaattaca ttccaggaag tgaactagta cgtggccgtg gtggccctcg ttgtatgagt   1200
atgccacttt accgtgaaga tctttaa                                        1227
```

<210> SEQ ID NO 5
<211> LENGTH: 29
<212> TYPE: DNA
<213> ORGANISM: Artificial Sequence
<220> FEATURE:

```
<223> OTHER INFORMATION: Synthetic DNA

<400> SEQUENCE: 5
cgcggatcca tgagtcatcc aattaatgt                                              29

<210> SEQ ID NO 6
<211> LENGTH: 26
<212> TYPE: DNA
<213> ORGANISM: Artificial Sequence
<220> FEATURE:
<223> OTHER INFORMATION: Synthetic DNA

<400> SEQUENCE: 6
ccgctcgagt taaagatctt cacggt                                                 26

<210> SEQ ID NO 7
<211> LENGTH: 34
<212> TYPE: DNA
<213> ORGANISM: Artificial Sequence
<220> FEATURE:
<223> OTHER INFORMATION: Synthetic DNA

<400> SEQUENCE: 7
cttggctttt gatatccctg aacatcgtaa attc                                        34

<210> SEQ ID NO 8
<211> LENGTH: 32
<212> TYPE: DNA
<213> ORGANISM: Artificial Sequence
<220> FEATURE:
<223> OTHER INFORMATION: Synthetic DNA

<400> SEQUENCE: 8
gatatcaaaa gccaagatat ttttgaatcc ta                                          32
```